United States Patent [19]

Kenyon et al.

[11] Patent Number: 5,279,656
[45] Date of Patent: Jan. 18, 1994

[54] XANTHENE DYES FOR INK JET PRINTING

[75] Inventors: Ronald W. Kenyon, Failsworth; Peter Gregory, Bolton, both of England

[73] Assignee: Imperial Chemical Industries PLC, London, England

[21] Appl. No.: 973,666

[22] Filed: Nov. 9, 1992

[30] Foreign Application Priority Data

Nov. 15, 1991 [GB] United Kingdom ............... 9124300
Jun. 25, 1992 [GB] United Kingdom ............... 9213476

[51] Int. Cl.$^5$ ................... C09D 11/02; C07D 311/88
[52] U.S. Cl. .......................... 106/22 H; 106/22 K; 549/227; 549/394
[58] Field of Search ..... 106/22.H, 22.K; 549/227, 394

[56] References Cited

U.S. PATENT DOCUMENTS

| | | | |
|---|---|---|---|
| 3,708,499 | 1/1973 | Andree et al. | 106/22 H |
| 3,713,770 | 1/1973 | Mundlos et al. | 549/227 |
| 3,883,529 | 5/1975 | Austin | 549/394 |
| 4,386,216 | 5/1983 | Locatell, Jr. et al. | 549/394 |
| 4,581,071 | 4/1986 | Akutsu et al. | 106/22 H |

FOREIGN PATENT DOCUMENTS

| | | |
|---|---|---|
| 60-190478 | 9/1985 | Japan . |
| 631039 | 10/1949 | United Kingdom . |
| 631040 | 10/1949 | United Kingdom . |

OTHER PUBLICATIONS

'Kunstliche Organische Farbstoffe und Ihre Zwischenproducte', 1964, pp. 272-275.
'Synthetuc Dyes', Venkataraman, vol. II, 1952, pp. 752-755.

Primary Examiner—Helene Klemanski
Attorney, Agent, or Firm—Cushman, Darby & Cushman

[57] ABSTRACT

A compound of Formula (1):

wherein:
$X^1$ is a sulpho or carboxy group;
each $X^2$ independently is a substituent;
m has a value of from 0 to 2;
$Y^1$ and $Y^2$ are each independently alkyl or halo; and
Z is a carboxy group.

The above compounds may be used as colorants for ink jet printing inks either alone or as a mixture with a second magenta compound.

15 Claims, No Drawings

XANTHENE DYES FOR INK JET PRINTING

This invention relates to xanthene compounds having two or more carboxy groups and to processes for their preparation and use in inks, particularly inks used in ink jet printing.

According to the present invention there is provided a compound of Formula (1):

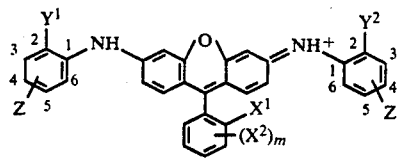

wherein:
$X^1$ is a sulpho or carboxy group;
each $X^2$ independently is a substituent;
m has a value of from 0 to 2;
$Y^1$ and $Y^2$ are each independently alkyl or halo; and
Z is a carboxy group.

When $X^1$ is a sulpho group it is preferred that at least one Z is at the 3-, 4- or 5-position.

When $X^1$ is a carboxy group it is preferred that one or both of the groups represented by Z are at the 3-, 4- or 5-position, more preferably at the 3- or 5-position because we have found that such compounds generally have better solubility in aqueous media than analogous compounds wherein the groups represented by Z are at the 4- or 6-position.

It is preferred that $X^1$ is a carboxy group.

The nature and position of the substituent or substituents defined by $-(X^2)m$ is generally selected on the basis of synthetic convenience. It is preferred that each $X^2$ independently contains less than 7 carbon atoms. As examples of substituents represented by $X^2$ there may be mentioned halo, especially chloro; sulpho; alkyl, especially $C_{1-4}$-alkyl; alkoxy, especially $C_{1-4}$-alkoxy; and carboxy. It is preferred that m has a value of 1, more preferably 0.

As will be appreciated the compound of Formula (1) can exist in other tautomeric forms than that shown and these are intended to be included in the definition provided by Formula (1).

When $Y^1$ or $Y^2$ is an alkyl group it preferably has less than seven carbon atoms, and more preferably is $C_{1-4}$-alkyl, especially methyl. When $Y^1$ or $Y^2$ is halo it is preferably chloro. It is preferred that $Y^1$ and $Y^2$ are identical to each other.

It is preferred that one or both of the groups represented by Z are at the 5-position indicated in Formula (1).

The compound of Formula (1) preferably has at least as many carboxy groups as sulpho groups because such a compound has particularly good water fastness when printed on plain paper.

The carboxy and sulpho groups which may be present in the compound of Formula (1) can be in the free acid or ionised form and are preferably of the formula $-CO_2-M^+$ or $-SO_3-M^+$ wherein $M^+$ is a cation.

The cation represented by $M^+$ is preferably an alkali metal, substituted ammonium or $NH_4^+$. $M^+$ may be selected so as to give the compound of Formula (1) characteristics which are preferred in ink jet printing, such as reasonable solubility in aqueous media and good water fastness when printed on plain paper. For example, when both groups represented by Z in Formula (1) are at the 4- or 6-positions it is desirable to enhance solubility and so $M^+$ is preferably lithium or ammonium having four $C_{1-4}$-alkyl substituents. However, when one or both of the groups represented by Z are at the 3- or 5-position the nature of $M^+$ is less important and $M^+$ may be selected from any of the aforementioned cations, especially $NH_4^+$.

The substituted ammonium cation may be a quaternary ammonium group of the formula $+NQ_4$ in which each Q independently is an organic radical, or two or three Qs together with the nitrogen atom to which they are attached form a heterocyclic ring and all remaining Qs are selected from $C_{1-4}$-alkyl. Preferred organic radicals represented by Q are $C_{1-4}$-alkyl radicals, especially methyl radicals. Preferred heterocyclic rings formed by $+NQ_4$ are 5 or 6 membered heterocyclic rings.

As examples of quaternary ammonium groups of formula $+NQ_4$ there may be mentioned $N^+(CH_3)_4$, $N^+(CH_2CH_3)_4$, N-methyl pyridinium, N,N-dimethyl piperidinium and N,N-dimethyl morpholinium.

Alternatively the substituted ammonium cation may be a group of formula $+NHT_3$ wherein each T independently is H or $C_{1-4}$-alkyl provided at least one T is $C_{1-4}$-alkyl, or two or three groups represented by T together with the nitrogen atom to which they are attached form a 5 or 6 membered ring, especially a pyridine, piperidine or morpholine ring. As examples of groups of formula $+NHT_3$ there may be mentioned $(CH_3)_3N^+H$, $(CH_3)_2N^+H_2$, $H_2N^+(CH_3)(CH_2CH_3)$, $CH_3N^+H_3$, $CH_3CH_2N^+H_3$, $H_2N^+(CH_2CH_3)_2$, $CH_3CH_2CH_2N^+H_3$, $(CH_3)_2CHN^+H_3$, isopropyl ammonium, pyridinium, piperidinium and morpholinium.

It is preferred that the substituted ammonium cation is derived from an amine which is volatile under ambient conditions, i.e. an amine which has a vapour pressure of less than 60, preferably less than 20, at 20° C. and 760 mm Hg pressure.

As will be understood the positive charge shown in Formula (1) is balanced by a negative charge, for example when $X^1$, X or Z is in ionised form such as $-CO_2-$ or $SO_3-$.

The compounds of Formula (1) may be prepared by condensing together compounds of Formula (2), (3) and (4) wherein $X^2$, $Y^1$, $Y^2$ and Z are as hereinbefore defined and $X^3$ is C=O or $SO_2$:

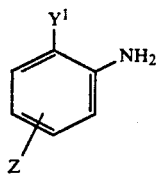

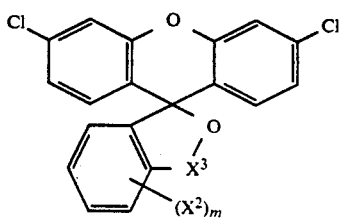

-continued

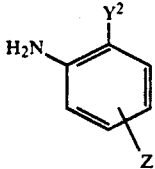

(4)

Condensation of compounds (2), (3) and (4) is preferably performed at a high temperature, more preferably above 150° C., especially in the range 170°-190° C. The condensation may be performed in a high boiling solvent, for example sulpholane.

When $X^3$ is $SO_2$ we have found that a compound of Formula (3) may be condensed in a step-wise manner with a compound of Formula (2) under mild conditions, followed by condensation with a compound of Formula (4) under more forcing conditions. This is of particular value where the compounds of Formula (2) and (4) are different to each other.

According to a second aspect of the present invention there is provided a process for the preparation of a compound of Formula (1), wherein $X^1$ is a sulpho group and $Y^1$, $Y^2$, Z, $X^2$ and m are as hereinbefore defined, comprising the steps:
(a) condensing a compound of Formula (2) with a compound of Formula (3) under mild conditions; and
(b) condensing a compound of Formula (4) with the product of step (a) under more forcing conditions than used in step (a) to give a compound of Formula (1);
Wherein the compounds of Formula (2), (3) and (4) are as hereinbefore defined, with the proviso that $X^3$ is $SO_2$.

Step (a) is preferably performed below 105° C., for example at 70°-90° C. It is convenient to perform step (a) in a protic or aprotic solvent, for example a $C_{1-4}$-alkanol.

Step (b) is preferably performed in the absence of solvent or using sulpholane as solvent (as this gives a better yield than when, for example, ethylene glycol or N-methyl pyrrolidone is used) together with a zinc halide, for example $ZnCl_2$. It is preferred that step (b) is performed above 150° C., especially in the range 170°-190° C.

The compounds of Formula (1) are especially useful for the preparation of inks, especially aqueous inks, used in ink jet printing and particularly thermal ink jet printing.

The compound of Formula (1) has an attractive bright magenta shade with particularly good water fastness and light fastness when printed on plain paper and may be used as a shading component for a second water-soluble magenta compound, that is to say a magenta compound which is not of Formula (1). The compound of Formula (1) has also been found to give prints on plain paper with sharply defined edges.

According to a further aspect of the present invention there is provided a composition comprising a compound of Formula (1) and a second water-soluble magenta compound.

The relative amounts of compound of Formula (1) and the second magenta compound may be varied between wide limits, preferably so as to ensure that the composition has acceptable brightness and light fastness for practical use in ink jet printing. It is preferred that the relative amounts (by weight) of compound of Formula (1) and the second magenta compound are in the range 95:5 to 5:95, more preferably 90:10 to 10:90, especially 60:40 to 40:60. The second water-soluble magenta compound is preferably not of Formula (1).

A preferred second magenta compound which may be mixed with the compound of Formula (1) is of Formula (5) or salt thereof:

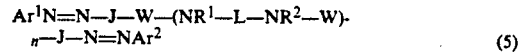

wherein:

J is

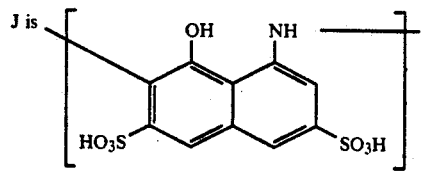

$Ar^1$ and $Ar^2$ are each independently aryl or substituted aryl providing at least one of $Ar^1$ and $Ar^2$ has at least one substituent selected from COOH and COSH;
each $R^1$ and $R^2$ is independently H, alkyl, substituted alkyl, alkenyl or substituted alkenyl;
L is a divalent organic linking group;
n is 0 or 1;
each W independently is carbonyl or a group of the formula (6), (7) or (8):

each B independently is $NR^3R^4$, $SR^5$ or $OR^5$;
each D independently is H, Cl, B, $SR^6$ or $OR^6$;
each E independently is Cl or CN;
$R^3$, $R^4$, $R^5$ and $R^6$ are each independently H, alkyl, substituted alkyl, alkenyl, substituted alkenyl, aryl, substituted aryl, aralkyl, substituted aralkyl or $R^3$ and $R^4$ together with the nitrogen atom to which they are attached form a 5 or 6 membered ring;
provided the compound of Formula (5) has at least as many groups selected from —COOH and —COSH as —$SO_3H$ groups.

It is preferred that the compound of Formula (5) has at least as many —COOH groups as —$SO_3H$ groups.

The groups $Ar^1$ and $Ar^2$ are preferably independently selected from optionally substituted naphthyl and optionally substituted phenyl, especially optionally substituted phenyl. The optional substituents on $Ar^1$ and $Ar^2$ are preferably selected from alkyl, especially $C_{1-4}$-alkyl;

alkoxy, especially $C_{1-4}$-alkoxy; —$SO_3H$; —$PO_3H_2$; —COSH; —OH; —$CO_2H$; halogen, especially Cl or Br; and optionally substituted $C_{1-4}$-alkyl. It is particularly preferred that when $Ar^1$ and $Ar^2$ are substituted the substituents are independently selected from $CO_2H$, COSH and $SO_3H$, especially $CO_2H$ and that at least one of $Ar^1$ and $Ar^2$ has at least one —$CO_2H$ substituent. In especially preferred structures, each of $Ar^1$ and $Ar^2$ has at least one —COOH substituent and more particularly at least two —COOH substituents as in, for example, dicarboxyphenyl.

It is preferred that the chromophores $Ar^1N=N$—J— and $Ar^2N=N$—J— are identical or similar such that they absorb approximately the same wavelength of light. It is also preferred that compound of Formula (5) is free from cellulose reactive groups.

When W is of Formula (7) it is preferred that B is attached to the carbon atom between the two ring nitrogen atoms and that D is para to B. Each W is preferably of Formula (6).

B is preferably $NR^3R^4$, especially $NHC_2H_4OH$, $N(C_2H_4OH)_2$, morpholino, $NH(C_{1-6}$-alkyl), NH—$(CH_2)_2$—$CO_2H$, mono- or di-carboxyanilino, $NH.C_6H_4.SO_3H$, $NHCH_2SO_3H$ or $NHCH_2C_6H_4CO_2H$.

Each $R^1$ and $R^2$ is preferably H, $C_{1-6}$-alkyl or substituted $C_{1-6}$-alkyl. It is preferred that when $R^1$ or $R^2$ is substituted, the substituents are selected from —OH, —COOH and —$SO_3H$. As examples of $R^1$ and $R^2$ there may be mentioned H, methyl, ethyl, propyl, butyl, pentyl, hexyl, 3,3,5-trimethylhexyl, 2-hydroxyethyl, and allyl.

$R^3$, $R^4$, $R^5$ and $R^6$ are preferably each independently selected from H, $C_{1-10}$-alkyl, substituted $C_{1-10}$-alkyl, phenyl, substituted phenyl, $(CH_2)_{1-4}$-phenyl and substituted $(CH_2)_{1-4}$-phenyl. When $R^3$, $R^4$, $R^5$ or $R^6$ are substituted it is preferred that the substituent is selected from —OH, —$CH_3$, —$OCH_3$, —$SO_3H$ and —$CO_2H$. When $R^3$ and $R^4$ together with the nitrogen radical to which they are attached form a 5 or 6 membered ring it is preferred that they form a morpholine, piperazine or piperidine ring.

The identity of the divalent organic linking group L is not critical providing it does not interfere with the performance of the compound. As examples of divalent organic linking groups represented by L there may be mentioned:

(a) divalent aliphatic radicals, preferably those containing from 2 to 6 carbon atoms, especially $C_{2-6}$-alkylene such as ethylene, trimethylene, propylene, tetramethylene, alpha:beta-dimethylethylene and hexamethylene radicals;

(b) divalent aromatic homocyclic radicals in which at least one of the terminal links is through an aliphatic carbon atom, for example as in the benzylene —$C_6H_4.CH_2$— or the xylylene —$CH_2C_6H_4CH_2$— group;

(c) divalent monocyclic or fused polycyclic aromatic radicals, for example optionally substituted phenylene, naphthylene, anthraquinonylene or fluorenylene series, such as

| | |
|---|---|
| 1,3- or 1,4-phenylene | 2-nitro-1,4-phenylene |
| 3-sulpho-1,4-phenylene | 4-methoxy-1,3-phenylene |
| 4-sulpho-1,3-phenylene | 4-nitro-1,3-phenylene |
| 2-carboxy-1,4-phenylene | 2-chloro-1,4-phenylene |
| 4-carboxy-1,3-phenylene | 3,7-disulpho-1,5-naphthylene |

-continued 2-methoxy-1,4-phenylene;

(d) divalent radicals wherein the terminal bonds are attached to carbon atoms of two phenyl or naphthalene nuclei which are joined together either through a direct link or through an atom or chain of atoms which may form a homocyclic or heterocyclic ring. Of this type, there may be mentioned as examples divalent radicals derived from

| | |
|---|---|
| diphenyl | azobenzene |
| diphenyloxide | diphenyloxadiazole |
| diphenylamine | benzanilide |
| diphenylsulphide | diphenylurea |
| diphenylsulphone | 1,2-bis(phenylcarbamyl)ethylene |
| diphenylmethane | 1,4-bis-(phenylcarbamyl)butadiene |
| diphenylketone | 1,2-bis-(phenylcarbamyl)ethane |
| diphenylethane | 1,3-bis-(phenylcarbamyl)propane |
| diphenylethylene and | 2,4-dianilino-s-triazine; |

(e) nuclear substituted derivatives of the above, for example, containing COOH, methyl, nitro and/or sulphonic acid and/or chlorine atoms as substituents in the phenyl or naphthalene nuclei.

Alternatively the group $NR^1LNR^2$ can be piperazine in which the two ring nitrogen atoms are bonded to the groups represented by W. It is also to be understood that whilst formulae (6), (7) and (8) are represented in neutral form, the present invention also covers the salts thereof the alkali metal, ammonium and substituted ammonium salts as hereinbefore described for the compounds of Formula (1).

The compound of Formula (5) may be prepared by a process comprising the steps:

(i) diazotisation of amines of formulae $Ar^1NH_2$ and $Ar^2NH_2$ with a diazotising agent such as $HNO_2$, in the cold and preferably below 5° C. to give the corresponding diazonium salts;

(ii) condensation of HJH with a compound of the formula halo-W-halo, preferably cyanuric chloride, preferably in the presence of base, to give a compound of formula HJ-W-halo in which W is as defined above except that B is Cl;

(iii) coupling each of the diazonium salts from (i) above with an equivalent of a compound of formula HJ-W-halo to give compounds of the formula $Ar^1N=N$—J—W—halo and $Ar^2N=N$—J—W—halo in which each W is the same or different to each other and in which each W is as defined above except that B is Cl;

(iv) the products from (iii) are each condensed with an amine of formula $NHR^1$—L—$NR^2H$;

(v) condensation of the product from (iv) with a compound of formula BH, preferably in the presence of base;

wherein $Ar^1$, $Ar^2$, J, W, L, $R^1$, $R^2$ and B are as defined above unless otherwise stated.

As examples of amines of formulae $Ar^1NH_2$ and $Ar^2NH_2$ which may be used in the preparation of compounds of Formula (5), there may be mentioned

| | |
|---|---|
| 2-aminoisophthalic acid | 3-amino-4-fluorobenzoic acid |
| 4-aminoisophthalic acid | 3-amino-5-hydroxybenzoic acid |
| 5-aminoisophthalic acid | 3-amino-4-hydroxybenzoic acid |
| 3-aminophthalic acid | 3-amino-2-hydroxybenzoic acid |

-continued

| | |
|---|---|
| 4-aminophthalic acid | 2-amino-6-hydroxybenzoic acid |
| 2-aminoterephthalic acid | 2-amino-4-nitrobenzoic acid |
| 3-aminobenzoic acid | 3-amino-5-nitrobenzoic acid |
| 4-aminobenzoic acid | 2-nitro-3-aminobenzoic acid |
| anthranilic acid | 2-nitro-5-aminobenzoic acid |
| 4-sulphoanthranilic acid | 3-nitro-4-aminobenzoic acid |
| 5-sulphoanthranilic acid | 3-acetylamino-5-aminobenzoic acid |
| 2-amino-4-chlorobenzoic acid | 3-amino-4-methylbenzoic acid |
| 2-amino-5-chlorobenzoic acid | 2-amino-3-methylbenzoic acid |
| 3-amino-4-chlorobenzoic acid | 3-amino-4-methoxybenzoic acid |
| 5-amino-5-chlorobenzoic acid | 3-amino-4-hydroxybenzoic acid |
| 2-amino-5-methylbenzoic acid | 4-aminosalicylic acid |
| 2-amino-6-methylbenzoic acid | 5-aminosalicylic acid |
| 2-amino-5-bromobenzoic acid | 3-amino-2-naphthoic acid |
| 2-n-butoxy-4-aminobenzoic acid | 5-amino-2-naphthoic acid |
| | 8-amino-2-naphthoic acid |

The magenta compound of Formula (5) has particularly high light fastness when printed on plain paper and the compound of Formula (1) has particularly good brightness. By appropriate selection of the relative amounts of the magenta compound of Formula (5) and compound of Formula (1), for example in relative amounts as hereinbefore described, compositions may be prepared which combine the best features of each compound to give prints having both high light fastness and good brightness.

The present invention also provides an ink comprising a compound or composition according to the present invention and a liquid medium, preferably an aqueous medium. It is preferred that the compound or composition is completely dissolved in the liquid medium to form a solution.

The ink preferably contains from 0.5% to 20%, more preferably from 0.5% to 15%, especially up to 5%, more especially 1-2% by weight of the compound or composition, based on the total weight of the ink.

The ink preferably contains less than 5%, more preferably than 1% by weight of inorganic salts.

The liquid medium is preferably water or a mixture comprising water and a water-soluble organic solvent, preferably in a weight ratio from 99:1 to 1:99, more preferably from 95:1 to 50:50 and especially from 90:10 to 60:40.

The water-soluble organic solvent is preferably a $C_{1-4}$-alkanol such as methanol, ethanol, n-propanol, isopropanol, n-butanol, sec-butanol, tert-butanol or isobutanol; an amide such as dimethylformamide or dimethylacetamide; a ketone or ketone alcohol such as acetone or diacetone alcohol; an ether such as tetrahydrofuran or dioxane; a polyalkylene glycol such as polyethylene glycol or polypropylene glycol; an alkylene glycol or thioglycol containing a $C_2$–$C_6$ alkylene group such as ethylene glycol, propylene glycol, butylene glycol or triethylene glycol; a thiodiglycol, hexylene glycol, or diethylene glycol; a polyol such as glycerol or 1,2,6-hexanetriol; a lower alkyl ether of a polyhydric alcohol such as 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)ethoxy]ethanol; 2-pyrrolidone or N-methylpyrrolidone; or a mixture containing two or more of the aforementioned water-soluble organic solvents.

Preferred water-soluble organic solvents are selected from 2-pyrrolidone, N-methylpyrrolidone, an alkylene glycol or lower alkyl ether of a polyhydric alcohol such as ethylene glycol, diethylene glycol, triethylene glycol or 2-methoxy-2-ethoxy-2-ethoxyethanol; and a polyethylene glycol with a molecular weight of up to 500. A preferred specific solvent mixture is a binary mixture of water and either diethylene glycol, 2-pyrrolidone or N-methylpyrrolidone in a weight ratio as mentioned above.

Examples of suitable ink media are given in U.S. Pat. Nos. 4,703,113, 4,626,284 and EP 4,251,50A.

It is preferred that the inks of the present invention further comprise one or more of a penetrant to assist permeation of the dye into a paper substrate, a kogation-reducing agent to prevent or reduce the build-up of residue (koga) on the resistor surface in thermal ink jet printers and a buffer such as sodium borate, to stabilise the pH of the ink.

The kogation-reducing agent is preferably an oxo anion, such as described in EP 425150A. The oxo-anion may be $C_2O_4^{2-}$, $SO_3^{2-}$, $SO_4^{2-}$, molybdate, $AsO_4^{3-}$ or more preferably a phosphate ester, a diorganophosphate or more especially a phosphate salt which is particularly effective in reducing kogation.

The kogation-reducing agent is preferably present in the ink at a concentration from 0.001% to 15%, based on oxo-anion, and more preferably from 0.01% to 1% (by weight).

A further aspect of the present invention provides a process for printing a substrate with an ink using an ink jet printer, characterised in that the ink contains at least one compound and composition according to the present invention.

A suitable process for the application of an ink as hereinbefore defined comprises forming the ink into small droplets by ejection from a reservoir through a small orifice so that the droplets of ink are directed at a substrate. This process is commonly referred to as ink jet printing, and the ink jet printing processes for the present inks are preferably piezoelectric ink jet printing, and more especially thermal ink jet printing. In thermal ink jet printing, programmed pulses of heat are applied to the ink by means of a resistor, adjacent to the orifice during relative movement between the substrate and the reservoir.

A preferred substrate is an overhead projector slide or a cellulosic substrate, especially plain paper, which may have an acid, alkaline or neutral character.

The preferred ink used in the process is as hereinbefore described.

According to a still further aspect of the present invention there is provided a paper or an overhead projector slide printed with a compound or composition according to the invention.

The invention is further illustrated by the following Examples in which all parts and percentages are by weight unless otherwise indicated.

EXAMPLE 1

Preparation of the compound of Formula (9) where X is carboxy and $Q^1$ and $Q^2$ are both 2-methyl-5-carboxyphenyl

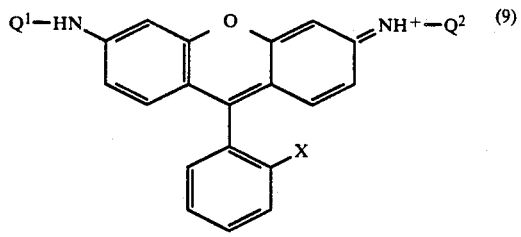

A mixture of 3,6-dichlorofluoran (7.4 g), 3-amino-4-methylbenzoic acid (9.1 g), zinc chloride (4.2 g) and sulpholane (20 g) was stirred at 180° C. for 3 hours. After cooling, the mixture was added to ice/water (200 g) and concentrated hydrochloric acid (10 ml) was added. The resultant precipitate was filtered off and washed with water.

The precipitate was added to water (600 ml) and the pH adjusted to 9.0–9.5 by addition of sodium hydroxide solution. The solution was screened and the filtrate acidified to pH 3 with concentrated hydrochloric acid. The title product in the free acid form was filtered off and washed with a little water to give a solid.

The solid was added to water (600 ml) and concentrated ammonium hydroxide added to pH 9–9.5. The solution was dialysed until no further chloride ion was detected, the solution was screened, and the water evaporated to give the title compound as the ammonium salt.

When made into an ink by dissolution of 1 part of the title compound in water/diethylene glycol (92.5/7.5) and printed onto plain paper using a thermal ink jet printer the title product as the ammonium salt gave bright magenta shades having high water fastness and good light fastness.

Further inks containing the title dye may be prepared according to the following formulations shown in Table I and Table II wherein figures denote parts by weight for each stated component:

The following Abbreviations are used:
PG=propylene glycol,
DEG=diethylene glycol,
NMP=N-methyl pyrollidone,
DMK=dimethylketone,
IPA=isopropanol,
MEOH=methanol,
2P=2-pyrollidone,
MIBK=methylisobutyl ketone,
P12=Propane-1,2-diol,
BDL=Butane-2,3-diol,
CET=Cetyl ammonium bromide,
PHO=$Na_2HPO_4$,
TBT=Tertiary butanol,
OXA=Oxalic acid.

TABLE I

| Ink No. | Dye Content | Water | PG | DEG | NMP | DMK | NaOH | Na Stearate | IPA | MEOH | 2P | MIBK |
|---|---|---|---|---|---|---|---|---|---|---|---|---|
| 1 | 2.0 | 80 | 5 | | 6 | 4 | | | | | 5 | |
| 2 | 3.0 | 90 | | 5 | 5 | | 0.2 | | | | | |
| 3 | 1.0 | 85 | 5 | | 2 | 2 | | 0.1 | | 5 | 1 | |
| 4 | 2.1 | 91 | | 8 | | | | | | | | 1 |
| 5 | 3.1 | 86 | 5 | | | | | 0.2 | 4 | | | 5 |
| 6 | 1.1 | 81 | | | 9 | | 0.5 | 0.5 | | | 9 | |
| 7 | 2.5 | 60 | 4 | 15 | 3 | 3 | | | 6 | 10 | 5 | 4 |
| 8 | 1.9 | 70 | | 20 | | | | | 10 | | | |
| 9 | 2.4 | 75 | 5 | 4 | | 5 | | | | 6 | | 5 |
| 10 | 4.1 | 80 | 3 | 5 | 2 | 10 | | 0.3 | | | | |
| 11 | 3.2 | 65 | | 5 | 4 | 6 | | | 5 | 4 | 6 | 5 |
| 12 | 4.6 | 96 | | | | | | | | 4 | | |
| 13 | 0.8 | 90 | 5 | | | | | | 5 | | | |
| 14 | 1.2 | 80 | 2 | 6 | 2 | 5 | | | 1 | | 4 | |
| 15 | 1.8 | 80 | | 5 | | | | | | | 15 | |
| 16 | 2.6 | 84 | | | 11 | | | | | | 5 | |
| 17 | 3.3 | 80 | 2 | | | 10 | | | | 2 | | 6 |
| 18 | 1.7 | 90 | | | 7 | | 0.3 | | 3 | | | |
| 19 | 1.5 | 69 | 2 | 20 | 2 | 1 | | | | | 3 | 3 |
| 20 | 1.6 | 91 | | | 4 | — | | | | | 5 | |

TABLE II

| Ink No. | Dye Content | Water | PG | DEG | NMP | CET | TBT | OXA | BDL | PHO | 2P | P12 |
|---|---|---|---|---|---|---|---|---|---|---|---|---|
| 21 | 3.0 | 80 | 15 | | | 0.2 | | | | | 5 | |
| 22 | 2.0 | 90 | | 5 | | | | | | 1.2 | | 5 |
| 23 | 1.5 | 85 | 5 | 5 | | 0.15 | 5.0 | 0.2 | | | | |
| 24 | 2.5 | 90 | | 6 | 4 | | | | | 0.12 | | |
| 25 | 3.1 | 82 | 4 | 8 | | 0.3 | | | | | | 6 |
| 26 | 0.9 | 85 | | 10 | | | | | 5 | 0.2 | | |
| 27 | 1.5 | 90 | | 5 | 5 | | 0.3 | | | | | |
| 28 | 2.9 | 70 | | 10 | 4 | | | | 1 | | 4 | 11 |
| 29 | 2.2 | 75 | 4 | 10 | 3 | | | | 2 | | 6 | |
| 30 | 2.6 | 91 | | 6 | | | | | | | | 3 |
| 31 | 3.2 | 76 | | 9 | 7 | | 3.0 | | | 0.95 | 5 | |
| 32 | 4.0 | 78 | 5 | 11 | | | | | | | | 6 |
| 33 | 3.3 | 86 | | | 7 | | | | | | 7 | |
| 34 | 1.1 | 70 | 5 | 5 | 5 | 0.1 | 0.2 | 0.1 | 5 | 0.1 | 5 | 5 |

EXAMPLE 2

Preparation of the compound of Formula (9) where X is carboxy and $Q^1$ and $Q^2$ are both 2-methyl-3-carboxyphenyl The method of Example 1 was repeated except that in place of 3-amino-4-methylbenzoic acid there was used an equivalent amount of 3-amino-2-methylbenzoic acid.

The ammonium salt of the title compound was made into an ink by dissolving 2 parts thereof in water/diethylene glycol (90:10) and was printed onto plain paper using a thermal ink jet printer to give bright magenta prints with high water fastness and good light fastness.

Further inks may be prepared according to the formulations described in Example 1, Tables I and II, except that in place of the dye from Example 1 there is used an equivalent amount of the dye from the present example.

EXAMPLE 3

Preparation of the compound of Formula (9) where X is sulpho and $Q^1$ and $Q^2$ are both 2-methyl-5-carboxyphenyl A mixture of 3,6-dichlorosulphonefluorescein (8.1 g), 3-amino-4-methylbenzoic acid (9.1 g), zinc chloride (4.2 g) and sulpholane (20 ml) was stirred at 175°–185° C. for 3 hours. After cooling, the mixture was added to ice-/water (100 g), stirred for 10 minutes and the precipitate filtered off.

The precipitate was dissolved in water (400 ml) by addition of sodium hydroxide solution to pH 9–10, screened free from insoluble material and the solution added to a mixture of water (400 ml) and concentrated hydrochloric acid (40 ml). The title product, in the form of the free acid, was filtered off, washed with a little water, pulled dry and re-dissolved in water (400 ml) by addition of ammonium hydroxide solution to pH 9. The solution was dialysed until no further chloride ion could be detected, screened and dried to give the title product as the ammonium salt.

An ink was made by dissolving 1 part of the title product (ammonium salt) in a mixture of diethylene glycol (10 parts) and water (90 parts) and adjusting the pH to 8.5–9.0 with ammonium hydroxide. When printed onto plain paper using a thermal ink jet printer the ink gave bright magenta prints having very good water fastness and good light fastness.

Further inks may be prepared according to the formulations described in Example 1, Tables I and II, except that in place of the dye from Example 1 there is used an equivalent amount of the dye from the present example.

EXAMPLE 4

Preparation of the compound of Formula (9) where X is sulpho, $Q^1$ is 2-methyl-5-carboxyphenyl and $Q^2$ is 2-methyl-6-carboxyphenyl Step (a)

A mixture of 3,6-dichlorosulphonefluorescein (i.e., the compound of Formula (2) wherein X is $SO_2$ and m has a value of 0) (2.0 g), 2-amino-3-methylbenzoic acid (0.7 g), ethanol (50 ml) and water (10 ml) was heated under reflux, with stirring, for 1 hour to give an orange solution. The orange solution was cooled and added to ice/water (250 ml) and stirred for ½ hour to give a precipitate which was filtered off, washed with a little water and dried.

Step (b)

A mixture of the product from step (a) (1.3 g), 3-amino-4-methylbenzoic acid (0.4 g), zinc chloride (0.5 g) and sulpholane (10 ml) was stirred at 175°–185° C. for 3 hours. After cooling, the mixture was added to water (250 ml), stirred for 15 minutes and the precipitate filtered off. The precipitate was re-dissolved in water (200 ml) by addition of sodium hydroxide solution to pH 9.0, screened to remove insoluble material, and added to water (200 ml) and concentrated hydrochloric acid (20 ml). The title product was filtered off, added to water (200 ml) and the pH adjusted to 9 by addition of ammonium hydroxide solution. The solution was dialysed until no further chloride was detected, screened and dried to give the ammonium salt of the title compound.

An ink was made by dissolving 1 part of the ammonium salt of the title product in a mixture of diethylene glycol (15 parts) water (85 parts) and adjusting the pH to 8.5–9.0 with ammonium hydroxide. When printed onto plain paper using a thermal ink jet printer the ink gave bright magenta prints having very good water fastness and good light fastness.

Further inks may be prepared according to the formulations described in Example 1, Tables I and II, except that in place of the dye from Example 1 there is used an equivalent amount of the dye from the present example.

EXAMPLE 5

A composition was prepared comprising 1 part of the title compound of Example 1 (ammonium salt) and 1 part of the compound of Formula (10) wherein Z is $NH(CH_2)_2OH$:

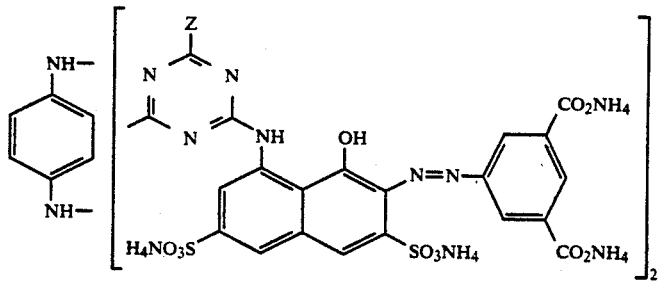

An ink was prepared comprising a mixture of 2 parts of the composition, water (92.5 parts) and diethylene glycol (7.5 parts). When printed onto plain paper using a thermal ink jet printer the ink gave prints having a magenta shade with very high waterfastness and very good light fastness.

Further inks may be prepared according to the formulations described in Example 1, Tables I and II, except that in place of the dye from Example 1 there is used an equivalent amount of the composition from the present example.

EXAMPLE 6

A composition was prepared comprising 1.6 parts of the title compound of Example 1 (ammonium salt) and 0.4 parts of the compound of Formula (10) wherein Z is $NH_2$.

An ink was prepared comprising 2 parts of the composition, water (87.5 parts) and diethylene glycol (12.5 parts) when printed onto plain paper the ink gave bright magenta prints with high waterfastness and good light fastness.

Further inks may be prepared according to the formulations described in Example 1, Tables I and II, except that in place of the dye from Example 1 there is used an equivalent amount of the composition from the present example.

EXAMPLE 7

Example 1 was repeated to give the title product which, after acidification to pH 3 with conc HCl, was in the free acid form. This product was filtered off, washed with water, added to water (600 ml) and basified to pH 9-9.5 using 40% aqueous dimethylamine. The resultant solution was dialysed until no further chloride ions could be detected, the solution screened and water evaporated to give the title dye of Example 1 in the form of its dimethylammonium salt (hereinafter EX1DMA).

An ink was prepared by dissolving 2 parts of EX1DMA in water/diethylene glycol (92.5/7.5) and printed on plain paper using a thermal ink jet printing machine. The resultant images had a bright magenta shade and high water fastness.

Further inks including EX1DMA dye may be prepared according to the following formulations:

| Ink | Dye Content (parts) | Liquid medium and other components (parts) |
| --- | --- | --- |
| 1 | 2.5 | Water (60) |
|   |     | Ethylene glycol (40) |
| 2 | 4.0 | Water (85) |
|   |     | Diethylene glycol (10) |
|   |     | 2-pyrollidone (5) |
| 3 | 1.0 | Water (90) |
|   |     | Diethylene glycol (10) |
|   |     | Sodium oxalate (0.2) |
| 4 | 3.0 | Water (65) |
|   |     | Glycerol (25) |
|   |     | Triethanolamine (10) |
|   |     | Sodium borate (0.2) |
| 5 | 2.0 | Water (80) |
|   |     | Ethylene glycol (15) |
|   |     | N-methyl pyrollidone (5) |

We claim:

1. A compound of Formula (1):

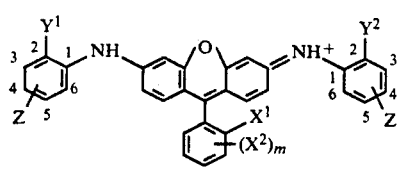

(1)

wherein:

$X^1$ is a sulpho or carboxy group;
each $X^2$ independently is a substituent;
m has a value of from 0 to 2;
$Y^1$ and $Y^2$ are each independently alkyl or halo; and
Z is a carboxy group.

2. A compound according to claim 1 wherein $X^1$ is a carboxy group.

3. A compound according to claim 1 or claim 2 wherein $Y^1$ and $Y^2$ are each independently $C_{1-4}$-alkyl or halo.

4. A compound according to claim 1 wherein one or both of the groups represented by Z are at the 3- or 5-position.

5. A compound according to claim 1 wherein $X^2$ contains less than 7 carbon atoms.

6. A compound of Formula (1):

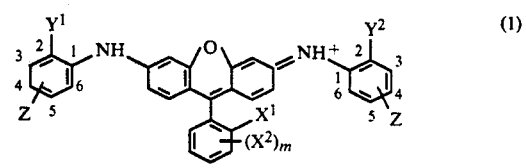

(1)

wherein:

$X^1$ is a sulpho or carboxy group;
each $X^2$ independently is halo, sulpho, $C_{1-4}$-alkyl, $C_{1-4}$-alkoxy or carboxy;
m has a value of from 0 to 2;
$Y^1$ and $Y^2$ are each independently $C_{1-4}$-alkyl or halo; and
Z is a carboxy group.

7. A compound according to claim 6 wherein the carboxy and sulpho groups are of formula $-CO_2^-M^+$ or $-SO_3^-M^+$ wherein $M^+$ is an alkali metal, substituted ammonium or $NH_4^+$.

8. A compound according to claim 6 wherein the carboxy and sulpho groups are of formula $-CO_2^-M^+$ or $-SO_3^-M^+$ wherein $M^+$ is an alkali metal, ammonium or a group selected from the group consisting of $(CH_3)_3N^+H$, $(CH_3)_2N^+H_2$, $H_2N^+(CH_3)(CH_2CH_3)$, $CH_3N^+H_3$, $CH_3CH_2N^+H_3$, $H_2N^+(CH_2CH_3)_2$, $CH_3CH_2CH_2N^+H_3$, $(CH_3)_2CHN^+H_3$, isopropylammonium, pyridinium, piperidinium and morpholinium.

9. A composition comprising a compound according to claim 1 and a second water-soluble magenta compound in relative amounts, by weight, in the range 95:5 to 5:95.

10. A composition according to claim 9 wherein the second magenta compound is of Formula (5) or salt thereof:

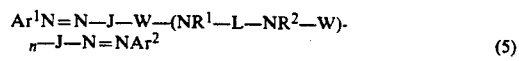

wherein:

J is

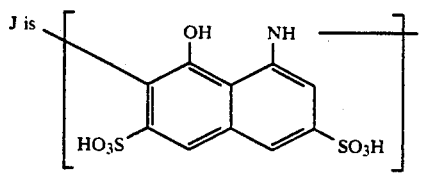

Ar¹ and Ar² are each independently aryl or substituted aryl providing at least one of Ar¹ and Ar² has at least one substituent selected from COOH and COSH;

each R¹ and R² is independently H, alkyl, substituted alkyl, alkenyl or substituted alkenyl;

L is a divalent organic linking group;

n is 0 or 1;

each W independently is carbonyl or a group of the formula (6), (7) or (8):

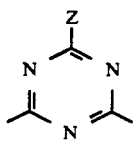
(6)

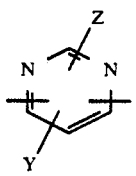
(7)

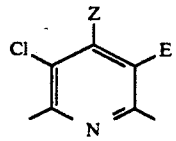
(8)

each B independently is $NR^3R^4$, $SR^5$ or $OR^5$;
each D independently is H, Cl, B, $SR^6$ or $OR^6$;
each E independently is Cl or CN;
$R^3$, $R^4$, $R^5$ and $R^6$ are each independently H, alkyl, substituted alkyl, alkenyl, substituted alkenyl, aryl, substituted aryl, aralkyl, substituted aralkyl or $R^3$ and $R^4$ together with the nitrogen atom to which they are attached form a 5 or 6 membered ring;
provided the compound of Formula (5) has at least as many groups selected from —COOH and —COSH as —SO₃H groups.

11. An ink comprising a compound according to claim 1 and a liquid medium.

12. A process for printing a substrate with an ink using an ink jet printer comprising forming the ink into small droplets by ejection from a reservoir through a small orifice so that the droplets of ink are directed at a substrate, wherein said ink is as defined in claim 11.

13. A paper or an overhead projector slide printed with a compound according to claim 1.

14. An ink comprising a composition according to claim 10 and a liquid medium.

15. A paper or an overhead projector slide printed with a composition according to alaim 9.

* * * * *